United States Patent [19]

Higuchi et al.

[11] 4,002,756
[45] Jan. 11, 1977

[54] USEFUL PRO-DRUG FORMS OF THEOPHYLLINE

[75] Inventors: Takeru Higuchi; Nicolae S. Bodor; Yu-Neng Kuo, all of Lawrence, Kans.

[73] Assignee: Interx Research Corporation, Lawrence, Kans.

[22] Filed: Sept. 26, 1975

[21] Appl. No.: 617,030

Related U.S. Application Data

[62] Division of Ser. No. 463,092, April 22, 1974, Pat. No. 3,935,196.

[52] U.S. Cl. .............................................. 424/253
[51] Int. Cl.[2] ...................................... A61K 31/52
[58] Field of Search ................. 424/253; 260/240 J, 260/256

[56] References Cited

UNITED STATES PATENTS

| | | | |
|---|---|---|---|
| 2,729,643 | 1/1956 | Stoll et al. | 260/256 |
| 3,935,196 | 1/1976 | Higuchi et al. | 260/256 |

Primary Examiner—Leonard Schenkman
Attorney, Agent, or Firm—John J. McDonnell

[57] ABSTRACT

There is provided novel and useful pro-drug forms of theophylline having the formula:

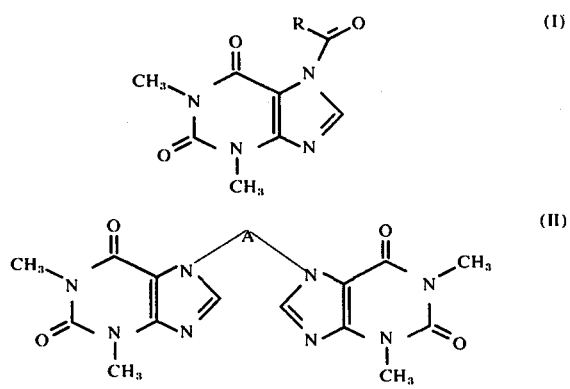

wherein R represents a member selected from the group consisting of a straight or branched $C_4$–$C_{20}$ alkyl group, a straight or branched $C_{14}$–$C_{20}$ alkenyl group, a substituted phenyl group or a substituted or unsubstituted naphthyl group whose substituents are selected from the group consisting of a hydroxy group, a $C_1$–$C_4$ alkyl group, a $C_1$–$C_4$ alkoxy group, a $C_1$–$C_4$ acyloxy group, and a halogen atom (Cl, Br, I), and a substituted or unsubstituted heteroaromatic group whose substituents are selected from the group consisting of a hydroxy group, a $C_1$–$C_4$ alkyl group, a $C_1$–$C_4$ alkoxy group, a $C_1$–$C_4$ acyloxy group, and a halogen atom (Cl, Br, I), and wherein A presents a member selected from the group consistng of a —CO— group, a —CO—$(CH_2)_n$—C—group, wherein n represents an integer of from 1 to 16, a —CO—CH=CH—CO— group (cis or trans),

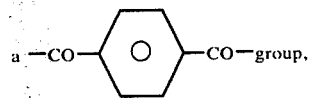

and a

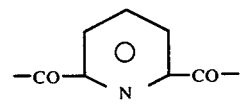

group.

The compounds of this invention are useful in the treatment of asthma in warm-blooded animals. Upon administration, the compounds of this invention slowly go into solution and subsequently cleave prior to and/or during the absorption process, releasing theophylline in a sustained manner at a non-toxic, therapeutic level; that is, without the large blood level variations normally observed when theophylline per se is administered.

4 Claims, 2 Drawing Figures

USEFUL PRO-DRUG FORMS OF THEOPHYLLINE

This is a division of application Ser. No. 463,092, filed Apr. 22, 1974 now U.S. Pat. No. 3,935,196.

BACKGROUND OF THE INVENTION

1. FIELD OF THE INVENTION

The present invention is directed to novel and useful derivatives of theophylline, a known drug useful in the treatment of asthma. More particularly, the present invention is directed to certain "pro-drug" forms of theophylline useful in the treatment of asthma in warm-blooded animals, e.g. humans.

For the purposes of this application, the term "pro-drug" denotes a derivative of a known and proven prior art compound (i.e., theophylline) which derivative, when administered to a warm-blooded animal, "cleaves" in such a manner as to release the proven drug form and permit the same to attain a sustained therapeutic level for a longer period of time than that which could be attained if the proven drug form per se was administered. More specifically, because of the very low water solubility and low dissolution rate of the pro-drug forms of this invention, such forms enable theophylline to be released quite slowly thus permitting therapeutic blood levels of the same to be maintained over an extended period of time, while at the same time, avoiding nontoxic blood levels of theophylline to be reached. The pro-drug forms of this invention are cleaved so rapidly in aqueous solution that the "pro-drug" form per se does not reach the bloodstream, but rather, cleavage of the pro-drug occurs before and/or during the absorption process. As such, substantial and sustained bioavailability is assured.

2. DESCRIPTION OF THE PRIOR ART

Theophylline, normally administered as the ethylenediamine salt (Aminophylline) or choline salt, is a useful and potent bronchodilator commonly prescribed for the treatment of bronchial asthma. Because it is readily soluble, Aminophylline has for many years been accepted as an effective bronchodilator when given orally. However, Aminophylline in solution becomes highly alkaline and is hydrolized by the gastric juice with resultant gastric irritation from the free theophylline liberated.

5 to 12 mcg./ml of whole blood or 10 to 25 mcg./ml of plasma are the relative blood levels of theophylline generally accepted as necessary to achieve effective bronchodilation. See, E. G. Truitt, V. A. McKusic, J. C. Krantz, Jr.; *Pharm. Exp. Ther.*, 100, 309 (1950) and M. Warwick Turner; Brit. Med. Jr., 2, 67 (1957), respectively. These theophylline blood levels are, however, difficult to attain, since as a result of the gastrointestinal upset experienced, patients cannot tolerate an adequate therapeutic dose of the drug. Reports in the literature with a variety of theophylline derivatives have often shown not only that theophylline blood levels achieved are below the values required for the relief of a bronchospasm, but also that even when these therapeutic levels are obtained, they fall off extremely rapidly in the first few hours following administration of the drug. Thus, repeated dosing of the patient about every 3 to 4 hours is necessary. See, E. G. Truitt, V. A. McKusic, J. C. Krantz, Jr., and M. Turner-Warwick, and R. H. Jackson, J. I. McHenry, S. B. Moreland, W. J. Raymer, and R. L. Etter; *Dis. Chest.*, 45, 75 (1964), and J. Schluger, J. T. McGuinn, and D. J. Hennesey; *Amer. J. Med. Sci.*: 233, 296 (1957), respectively.

In addition, even when therapeutic blood levels of theophylline are achieved, the amount of theophylline administered to a patient is so excessive that the therapeutic blood level achieved approaches and often reaches toxicity.

In one attempt to overcome the above disadvantages associated with administering theophylline, certain individuals have prepared a continuous-release formulation, such that the release rate of theophylline is dependent upon the formulation medium into which it is incorporated. That is, sustained therapeutic blood levels of theophylline are achieved through the use of a particular pharmaceutical formulation rather than chemical modification of the theophylline molecule. See, C. Boroda, R. B. Miller, S. T. Leslie, E. B. Nicol and I. Thompson; *Clin. Pharm.*, 383 (1973) and D. McIntosh, *Brit. J. Clin. Pharm.*, 12, 233 (1971) respectively.

Some theophylline derivatives, analogous to the compounds of formula (I) described hereinabove, have been prepared and described in the literature for the purpose of studying their chemistry per se, without any indication of any pharmaceutical utility. For instance, 7-acetyltheophylline was reported in three different articles. See, for instance, T. Higuchi, H. K. Lee and Ian H. Pittman; *Farm. Aikak.*, 80, 55 (1971) and Y. Ishido, A. Hosono, S. Isome, A. Maruyama, and T. Sato; *Bull. Chem. Soc. Japan*, 37, 1389 (1964), respectively.

7-acetyltheophylline and 7-benzoyltheophylline were reported in H. Biltz, and K. Struffe, Ann., 404, 170 (1914) as well.

7-propionyltheophylline and 7-butyryltheophylline have also been reported in the literature. See, Y. Ishido, A. Hosono, S. Isome, A. Maruyama, and T. Sato, supra.

Finally, U.S. Pat. No. 2,729,643 discloses certain 7-carboxamidotheophylline derivatives useful as diuretics.

As for the compounds of formula (II) described herein above, no prior art of structural chemical or pharmacological significance is known.

SUMMARY OF THE INVENTION

It is one object of the present invention to provide novel and useful pro-drug forms of theophylline, useful in the treatment of bronchial asthma in warm-blooded animals, e.g. humans.

It is another object of the present invention to provide novel and useful pro-drug forms of theophylline which cleave in such a manner as to enable the original proven drug form (theophylline) to be released when administered to a warm-blooded animal at a slow, but continual, non-toxic therapeutic level and to further permit the cleaved moiety (ies) unassociated with the proven drug form to be excreted without absorption or metabolized in a non-toxic fashion.

Still, it is another object of the present invention to provide novel and useful pro-drug forms of theophylline which because of their ability to cleave before and/or during the absorption process insure that substantial and sustained theophylline bioavailability as set forth above is attained.

Accordingly, all of the above objects are satisfied when employing a pro-drug of theophylline, having the formula I and II set out below:

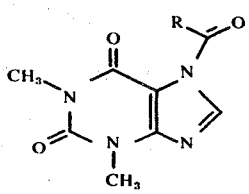

(I)

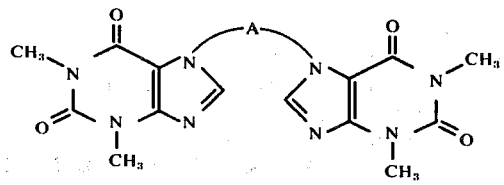

(II)

wherein R represents a member selected from the group consisting of a straight or branched $C_4$-$C_{20}$ alkyl group, a straight or branched $C_4$-$C_{20}$ alkenyl group, a substituted phenyl group or a substituted or unsubstituted naphthyl group whose substituents are selected from the group consisting of a hydroxy group, a $C_1$-$C_4$ alkyl group, a $C_1$-$C_4$ alkoxy group, a $C_1$-$C_4$ acyloxy group, and a halogen atom (Cl, Br, I), and a substituted or unsubstituted heteroaromatic group whose substituents are selected from the group consisting of a hydroxy group, a $C_1$-$C_4$ alkyl group, a $C_1$-$C_4$ alkoxy group, a $C_1$-$C_4$ acyloxy group, and a halogen atom (Cl, Br, I), and wherein A represents a member selected from the group consisting of a —CO— group, a —CO—$(CH_2)_n$—CO— group, wherein $n$ represents an integer of from 1 to 16, a —CO—CH=CH—CO— group (cis or trans), a

group, and a

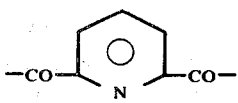

group.

In regard to the above generic formulae, the following remarks are pertinent from the standpoint of certain preferred embodiments relative to the substituents "R" and "A." When R represents an alkyl group (straight or branched) of from 4 to 20 carbon atoms, the odd numbered alkyl groups beginning with $C_7$ are preferred; when R represents an alkenyl group (straight or branched) of from 4 to 20 carbon atoms, the oleyl group is preferred; when R represents a substituted phenyl group, substituents in the 4-position with an alkoxy group of from 1 to 4 carbon atoms, or a 2-hydroxyphenyl group, or a 2-acyloxyphenyl of from 1 to 4 carbon atoms are preferred; and when R represents a heteroaromatic group, a 2-, 3-, or 4-pyridyl group or any equivalent analog thereof, such as a quinoline group is preferred.

With respect to substituent "A," when this substituent represents a —CO—$(CH_2)_n$—CO— group, wherein "$n$" represents an integer of from 1 to 16, the integer of from 1 to 4 is preferred; and when "A" represents a —CO—CH=CH—CO— group (cis or trans), the trans form if preferred.

As indicated earlier, all the compounds within the present invention satisfy the objectives noted above; however, certain compounds are preferred as set forth below:

1. 7-hexanoyltheophylline
2. 7-octanoyltheophylline
3. 7-decanoyltheophylline
4. 7-dodecanoyltheophylline
5. 7-myristyltheophylline
6. 7-palmityltheophylline
7. 7-stearyltheophylline
8. 7-[2-hydroxy]-benzoyltheophylline
9. 7-[2-acetyloxy]-benzoyltheophylline
10. 7,7'-carbonylditheophylline
11. 7,7'-succinylditheophylline
12. 7,7'-terephthaloylditheophylline
13. 7,7'-fumaroylditheophylline
14. 7,7'-glutarylditheophylline
15. 7,7'-adipylditheophylline

DETAILED DESCRIPTION OF THE INVENTION

Figure 1:
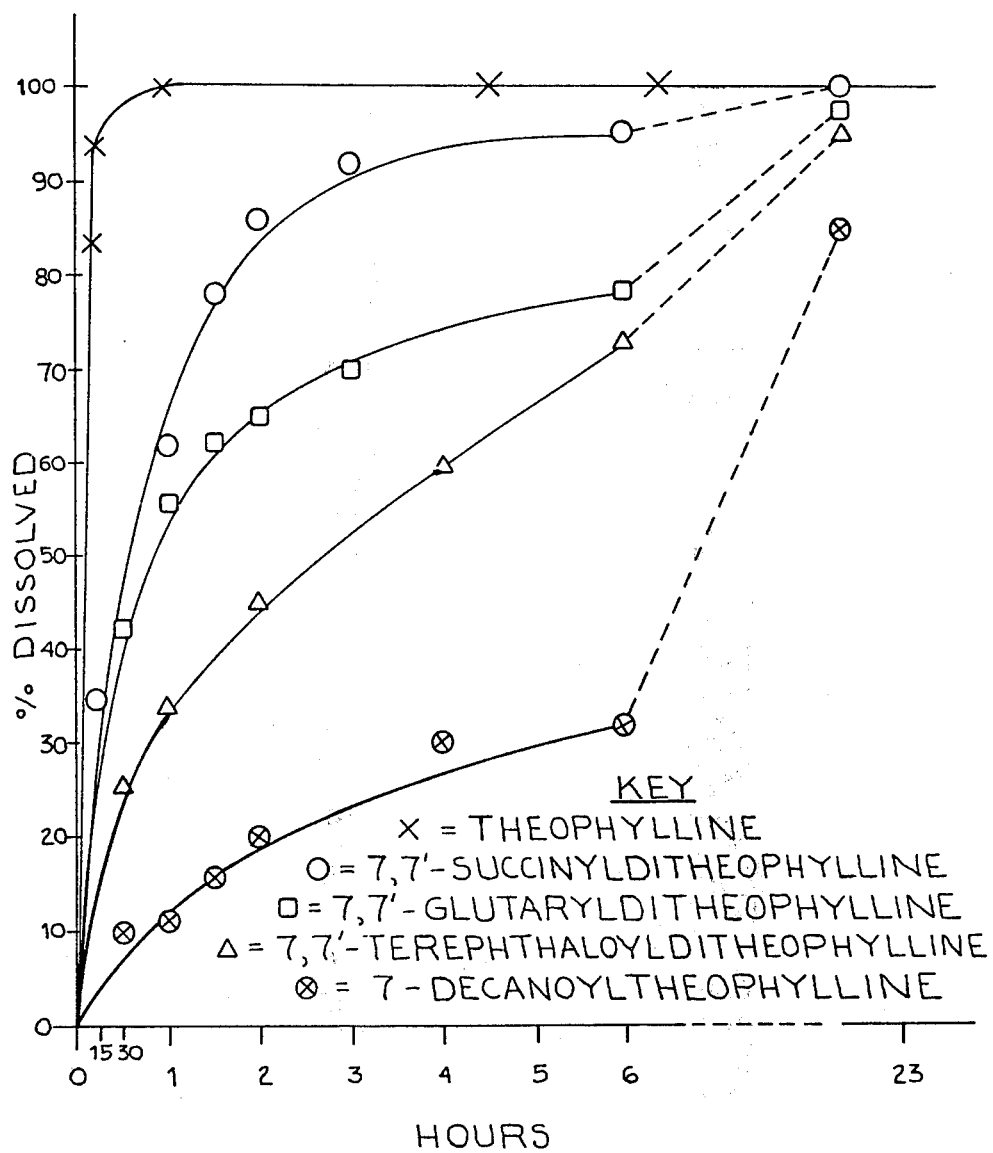

PREPARATION OF THE COMPOUNDS OF FORMULA (I):

Using stoichiometric amounts of each reactant, the compounds encompassed within Formula (I) can be prepared by any one of methods "A" through "C" described below:

A. Theophylline can be reacted with the appropriate corresponding acid anhydride wherein "R" is defined as above. The reaction is carried out in the presence of an inert organic solvent, such as benzene, toluene, a chlorinated hydrocarbon, e.g., 1,2-dichloroethane, dichloromethane, chloroform, or the like. The reaction is carried out at a temperature ranging from room temperature to 120° C (preferably, however, at the boiling point of a solvent employed), standard pressure and over a period of time ranging from 2 to 6 hours.

B. In one alternative procedure, theophylline can be reacted with the appropriate corresponding acyl halide (Cl, Br, I), wherein "R" is defined as above, in the presence of a suitable organic or inorganic base and in the presence of a suitable inert organic solvent. Illustrative organic or inorganic bases suitable for this reaction are pyridine, triethylamine, $K_2CO_3$, $Na_2CO_3$, etc. Illustrative inert organic solvents suitable for this reaction are benzene, toluene, xylene, and chlorinated hydrocarbons as illustrated in procedure (A) above. The reaction is advantageously carried out at a temperature range of from room temperature to 100° C (preferably at the boiling point of the solvent employed), standard pressure and over a reaction period of from 2 to 6 hours.

C. Alkali or alkaline earth metal salts of theophylline (Na, K, Li, Ca, Mg, etc.) or the thallous [Tl(1)] salt of theophylline can be reacted with the appropriate corresponding acyl halide as defined in procedure (B) above. The reaction is carried out in the presence of an inert organic solvent, such as ether, dioxane, tetrahydrofuran, 1,2-dimethoxyethane, etc. The reaction is advantageously carried out at room temperature, standard pressure, and for a period of time ranging from 2 to 6 hours.

Employing any one of the above procedures (A) through (C) above, the crude material obtained therefrom can be purified by way of recrystallization from an inert anhydrous organic solvent or mixtures of same, e.g., a hydrocarbon solvent such as hexane, heptane, petroleum ether, ligroin, etc., or an admixture of any of the above solvents with a chlorinated hydrocarbon solvent such as 1,2-dichloroethane, dichloromethane, etc.

PREPARATION OF THE COMPOUNDS OF FORMULA (II):

These compounds are prepared using procedures (A) or (B) listed above, with the exception that the appropriate acyl halide is substituted with the dihalide of the appropriate corresponding dicarboxylic acid.

Advantageously, in dealing with those dihalides which undergo side reactions, such as succinyl dihalide, fumaryl dihalide and the like, the temperature of the reaction will range from −78° C to room temperature. The pressure remains standard and the reaction time will be approximately 12 hours.

With respect to those dihalides which do not undergo side reactions, the reaction temperature will range from room temperature to 120° C, the pressure will remain standard and the reaction time will vary from 2 to 6 hours.

It should be emphasized that because of the nature of the reactions required to prepare compounds falling within formulae (I) and (II), it will be necessary to maintain strict anhydrous conditions throughout the synthesis. In addition, because of the stability problems incurred in storing such compounds following preparation, anhydrous storage conditions are also required.

Without further elaboration, it is believed that one of ordinary skill in the art can, using the proceeding description, utilize the present invention to its fullest extent. The following specific embodiments are, therefore, to be construed as merely illustrative, and not limitative of the remainder of the specification and claims in any way whatsoever.

EXAMPLE I

SYNTHESIS OF ILLUSTRATIVE THEOPHYLLINE DERIVATIVES 1. 7-octanoyltheophylline - 4.5 g (0.025 M) of theophylline was added to 200 ml of anhydrous 1,2-dichloroethane containing 5 ml (0.062 M) of pyridine. 4.86 g (0.013 M) of octanoyl chloride, diluted with 50 ml of 1,2-dichloroethane was then added to the solution. The mixture was heated under reflux for 2 hours and then cooled to 0° C. The precipitate formed was filtered and the filtrate was evaporated to dryness under a rotoevaporator. The crystals were recrystallized from heptane to give an essentially quantitative yield of the final compound, MP 62°–63° C. Anal. Calcd. for $C_{15}H_{22}N_4O_3$: C, 58.81; H, 7.28; N, 18.28. Found: C, 58.68; H, 7.24 N, 18.48.

2. Essentially quantitative yields of all the remaining theophylline derivatives of Formula (I) can be prepared by following the reaction scheme described in paragraph 1 above by simply substituting the appropriate acyl chloride

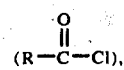

wherein R is as defined above. The following specific derivatives have been prepared in this manner:
A 7-pivaloyltheophylline
B 7-hexanoyltheophylline
C 7-decanoyltheophylline
D 7-oleoyltheophylline
E 7-palmitoyltheophylline
F 7 -myristyltheophylline
G 7-stearyltheophylline
H 7-[2-hydroxy]-benzoyltheophylline
I 7-[2-acetyloxy]-benzoyltheophylline 3. 7,7′-succinylditheophylline - 9 g. (0.05 M) of grounded theophylline was suspended in about 1 liter of anhydrous $CHCl_3$. The mixture was cooled to −20° to 40° C (dry ice - 1,2-dichloroethane bath). 3.8 g (0.0247 M) of succinyl chloride was diluted with 50 ml of anhydrous $CHCl_3$ and this solution was then added to the initial solution. 5 ml (0.062 M) of pyridine diluted in 50 ml of $CHCl_3$ was then added dropwise to the resulting solution. The solution was then stirred and maintained at a temperature of −20° to 40° C for a period of from 4 to 6 hours to give a white crystalline final product in essentially quantitative yield. The final product was then filtered and washed with anhydrous $CHCl_3$ (3 × 300 ml) to give an essentially quantitative yield of the final product, MP 266° C. Anal. Calcd for $C_{18}H_{18}N_8O_6$: C, 48,87; H, 4.10; N, 25.33. Found: C, 48.44; H, 4.19; N, 25.77.

4. By substituting the appropriate acyl chloride

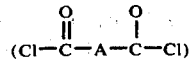

in the reaction scheme described in paragraph (3) above, wherein A is defined as above, the remaining 7,7′-ditheophylline derivatives of Formula (II) can be prepared in essentially quantitative yield. Illustrative compounds prepared in an analogous manner are:
A 7,7′-glutarylditheophylline
B 7,7′-terephthaloylditheophylline
C 7,7′-carbonylditheophylline
D 7,7′-fumaroylditheophylline In each of the above Examples I (1) – I (4), reference to "essentially quantitative" with respect to the yield of each final product denotes at least a 90–95% yield.

EXAMPLE II

DISSOLUTION RATE - THEOPHYLLINE v. THEOPHYLLINE DERIVATIVES OF THIS INVENTION

In FIG. 1 attached hereto, there is provided a plot of the dissolution rates for theophylline versus selected theophylline derivatives of the present application. The Examiner can readily observe that as compared to theophylline, the theophylline derivatives of the present application are much less soluble, thus permitting theophylline to be released in a controlled, non-toxic therapeutic amount over an extended period of time. On the other hand, with theophylline, the dissolution rate is so rapid that a non-toxic sustained therapeutic release cannot be achieved.

The dissolution studies were conducted directly in accordance with the guidelines set forth in United States Pharmacopeia XVIII (U.S.P.) at pages 934–935. The apparatus and materials employed were within U.S.P. requirements.

The dissolution rate of the drugs were run in 500 ml of distilled water containing two drops of Tween 80 in a standard dissolution pot at a temperature of 25° C (+ or − 0.5° C) via a constant temperature water bath. Samples of 100 to 200 mesh powder of each compound tested were transferred directly into the dissolution medium and stirred with a standard U.S.P. stainless steel paddle. The paddle was placed at the center of the 500 ml dissolution medium and rotated at a rate of 100 rpm. After a constant reading was obtained, the solution was sonicated for 15 minutes to obtain the infinite reading. All samples were run at least twice. The concentration of each sample in the dissolution medium never exceeded 5% of the solubility of theophylline.

EXAMPLE III

IN VIVO COMPARISON OF THEOPHYLLINE v. 7,7′-SUCCINYLDITHEOPHYLLINE

In order to determine the superiority of the theophylline derivatives of this invention over theophylline per se, the following in vivo study was carried out.

Beagle dogs of both sexes, weighing 10 to 15 Kg. were fasted for 12 hours prior to use. Theophylline (30 mg./Kg.) and 7,7′-succinylditheophylline (equivalent to 30 mg.kg. of theophylline) were suspended in 5% methylcellulose and administered orally via a conventional gastric delivery tube. Each suspended drug solution was prepared immediately prior to administration. 10 ml of blood was withdrawn from each dog immediately prior to drug administration. Then, blood samples consisting of 10 ml of blood were obtained at 15, 30, 60, 120, 240, 360, 480 and 720 minutes after drug administration. The plasma was separated conventionally and stored in a freezer pending assay. Theophylline concentrations in plasma were determined by the spectraphotometric method of Shack and Waxler*. 2 ml of plasma was acidified with 1 N HCl to a pH of 5.5—6 and then was extracted with 20 ml of organic phase, 5% isopropanol in chloroform. The organic phase was re-extracted with 3 ml of 1 N sodium hydroxide. The absorbance was determined with a 1 cm pathlength cell in a UV spectrophotometer (Carey 14).

*Shack, J. A. and Waxler, S. H., "An Ultraviolet Spectrophotometric Method for the Determination of Theophylline and Theobromine in Blood and Tissues, "J. Pharmacol. Exp. Ther. 97, 283-291 (1949).

Figure 2:
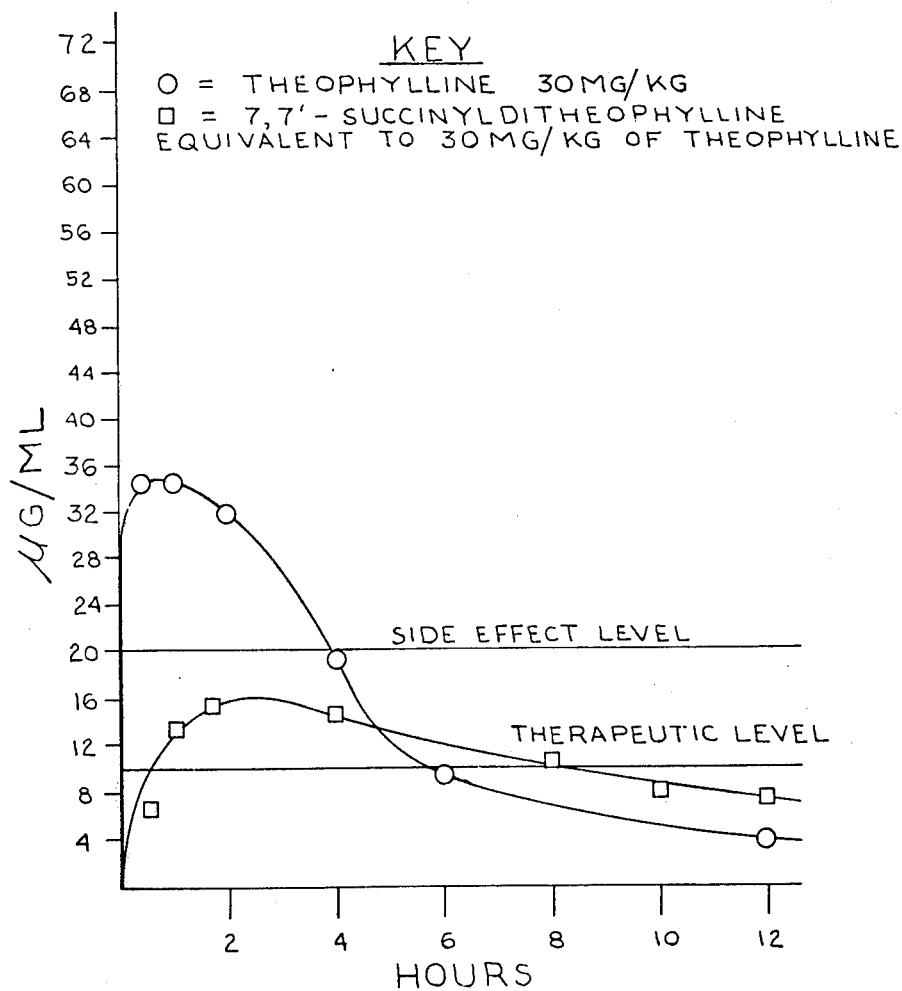

A plot of the results of this study is set forth in FIG. 2 attached. The results clearly establish the superiority of the pro-drug forms of this invention over theophylline from a nontoxic, sustained and controlled therapeutic release standpoint.

The results of the above study further demonstrate that the pro-theophylline derivatives of this invention can be tolerated even in higher doses other than that administered (30 mg/Kg. in comparison to theophylline per se without compromising the recited objectives of the invention.

When the remaining compounds of the present invention are subjected to in vivo testing as above, suitable sustained therapeutic levels of theophylline, within the intent and purpose of this invention will be obtained.

The pro-drug forms of this invention are suitably administered in oral dosage form, such as by tablet or capsule, by combining the same in a therapeutic amount with any oral pharmaceutically acceptable inert carrier, such as lactose, starch (pharmaceutical grade), dicalcium phosphate, calcium sulfate, Kaolin, Mannitol, and powdered sugar. In addition, when required, suitable binders, lubricants, disintegrating agents, and coloring agents can also be added. Typical binders include starch, gelatin, sugars, such as sucrose, molasses, and lactose, natural and synthetic gums such as acacia, sodium alginate, extract of Irish moss, carboxymethylcellulose, methylcellulose, and polyvinylpyrrolidone, polyethylene glycol, ethylcellulose and waxes. Typical lubricants for use in these dosage forms can include, without limitation, boric acid, sodium benzoate, sodium acetate, sodium chloride, leucine, and polyethylene glycol. Suitable disintegrators can include, without limitation, starch, methylcellulose, agar, bentonite, cellulose and wood products, alginic acid, guar gum, citris pulp, carboxymethylcellulose, and sodium lauryl sulfate. If desired, a conventionally pharmaceutically acceptable dye can be incorporated into the dosage unit form, i.e., any of the standard FD&C dyes.

Any skilled artisan can prepare these oral dosage forms by simply referring to the oral dosage form preparatory procedure outlined in "REMINGTON'S PHARMACEUTICAL SCIENCES," Fourteenth Edition (1970), pages 1659 through 1698 inclusive.

While the therapeutic dosage range for the compounds of this invention will vary with the size and needs of the patient, generally speaking, therapeusis on a daily basis is achieved by administering 10 mg. to 15 mg. per Kg. of body weight, about every 8 to 12 hours.

From the foregoing description, one skilled in the art can easily ascertain the essential characteristics of this invention, and without departing from the spirit and scope thereof, can make various changes and/or modifications to the invention for adapting it to various usages and conditions. As such, such changes and modifications are properly, equitably and intended to be, within the full range of equivalence of the following claims.

What we claim is:

1. A method for inducing a non-toxic, sustained therapeutically effective release of theophylline in the bloodstream of a warm-blooded animal which comprises:

administering thereto, a bronchodilating amount of a pro-drug of theophylline of the formula

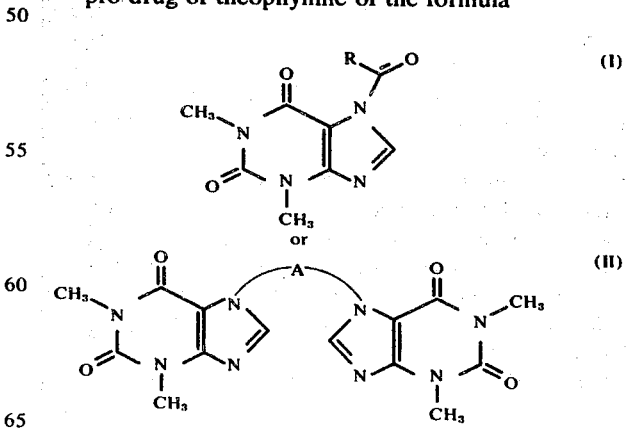

wherein R represents a member selected from the group consisting of straight or branched $C_4$-$C_{20}$ alkyl, straight or branched $C_4$-$C_{20}$ alkenyl, substituted phenyl or a substituted or unsubstituted naphthyl whose substituents are selected from the group consisting of hydroxy, $C_1$-$C_4$ alkyl, $C_1$-$C_4$ alkoxy, acyloxy derived from an alkanoic acid of up to 4 carbon atoms, chlorine, bromine, and iodine, 2,3,4 pyridyl or quinoline, and wherein A represents a member selected from the group consisting of —CO—, —CO—$(CH_2)_n$—CO— wherein $n$ represents an integer of from 1 – 16, —CO—CH=CH—CO—(cis or trans),

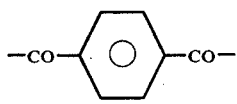

and

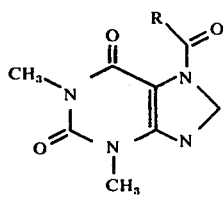

2. The method of claim 1, wherein said compound is: 7,7′-succinylditheophylline.

3. A pharmaceutical composition which comprises:
 1. a bronchodilating amount of a pro-drug of theophylline of the formula (I)

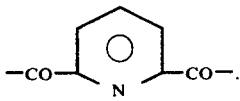

-continued
or

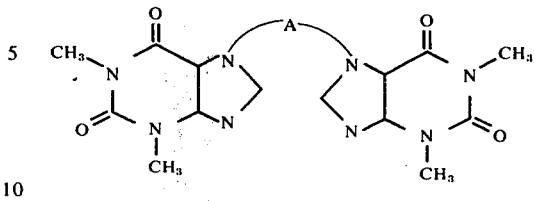

(II)

wherein R represents a member selected from the group consisting of straight or branched $C_4$-$C_{20}$ alkyl, straight or branched $C_4$-$C_{20}$ alkenyl, substituted phenyl or a substituted or unsubstituted naphthyl whose substituents are selected from the group consisting of hydroxy, $C_1$-$C_4$ alkyl, $C_1$-$C_4$ alkoxy, acyloxy derived from an alkanoic acid of up to 4 carbon atoms, chlorine, bromine, and iodine, 2,3,4 pyridyl or quinoline, and wherein A represents a member selected from the group consisting of —CO—, —CO—$(CH_2)_n$—CO— wherein n represents an integer of from 1-16, —CO—CH=CH—CO—(cis or trans),

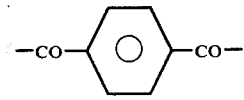

and

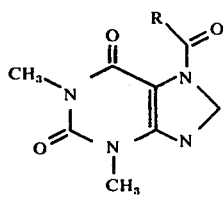

in combination with
 2. A pharmaceutically acceptable inert diluent.

4. A composition of claim 3, wherein said compound is: 7,7′-succinylditheophylline.

* * * * *